United States Patent [19]

Sahi

[11] Patent Number: 4,971,068
[45] Date of Patent: Nov. 20, 1990

[54] BLOOD VESSEL LOCATING NEEDLE ASSEMBLY WITH THERMOCHROMIC INDICATOR

[75] Inventor: Carl R. Sahi, Coventry, Conn.

[73] Assignee: Bio-Plexus, Inc., Tolland, Conn.

[21] Appl. No.: 376,420

[22] Filed: Jul. 7, 1989

[51] Int. Cl.⁵ .............................................. A61B 5/00
[52] U.S. Cl. .................................... 128/763; 604/116; 604/900; 128/771; 374/147
[58] Field of Search ............... 604/116, 168, 272, 318, 604/413, 404, 900; 128/736, 742, 763, 764, 771; 116/207; 374/147

[56] References Cited

U.S. PATENT DOCUMENTS

| | | | |
|---|---|---|---|
| 3,434,968 | 3/1969 | Barr, Sr. et al. | 604/413 X |
| 3,633,425 | 1/1972 | Sanford | 73/356 |
| 3,651,695 | 3/1972 | Brown | 374/147 |
| 3,886,930 | 6/1975 | Ryan . | |
| 3,889,658 | 6/1975 | Newhall | 128/736 |
| 3,926,368 | 12/1975 | Geen | 236/41 |
| 3,942,514 | 3/1976 | Ogle . | |
| 3,955,420 | 5/1976 | Parker | 116/207 X |
| 3,998,210 | 12/1976 | Nosari | 128/736 |
| 4,015,591 | 4/1977 | Suzuki et al. . | |
| 4,079,729 | 3/1978 | Cornell . | |
| 4,108,163 | 8/1978 | Fleckenstein et al. | 128/736 X |
| 4,108,175 | 8/1978 | Orton . | |
| 4,175,543 | 11/1979 | Suzuki et al. . | |
| 4,186,750 | 2/1980 | Patel | 128/748 |
| 4,215,699 | 8/1980 | Patel . | |
| 4,245,652 | 1/1981 | Kelly et al. | 128/736 |
| 4,280,508 | 7/1981 | Barrada . | |
| 4,281,543 | 8/1981 | Raz | 374/147 |
| 4,312,362 | 1/1982 | Kaufman . | |
| 4,413,633 | 11/1983 | Yanda | 128/736 |
| 4,416,290 | 11/1983 | Lutkowski . | |
| 4,436,098 | 3/1984 | Kaufman . | |
| 4,447,164 | 5/1984 | Berndt | 374/162 |
| 4,448,204 | 5/1984 | Lichtenstein . | |
| 4,476,877 | 10/1984 | Barker . | |
| 4,509,532 | 4/1985 | DeVries | 128/736 |
| 4,665,927 | 5/1987 | Daily . | |
| 4,679,571 | 7/1987 | Frankel et al. . | |
| 4,728,547 | 3/1988 | Vaz et al. . | |
| 4,827,944 | 5/1989 | Nugent | 128/771 |
| 4,846,005 | 7/1989 | Bacehowski et al. | 73/864.81 |

Primary Examiner—John D. Yasko
Assistant Examiner—Adam J. Cermak
Attorney, Agent, or Firm—Chilton, Alix & Van Kirk

[57] ABSTRACT

The penetration of a vein or the like by a fluid collecting or dispensing needle is rapidly confirmed by the transfer of thermal energy from fluid entering the needle bore upon such penetration to a temperature responsive medium in intimate contact with the exterior of the needle. The temperature responsive medium may comprise thermochromic liquid crystals which signal a change in temperature from ambient temperature by changing color.

4 Claims, 1 Drawing Sheet

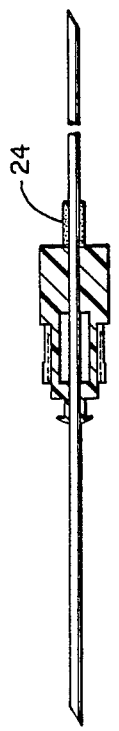
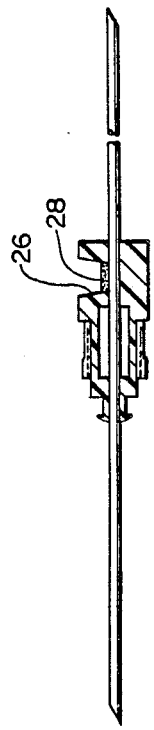
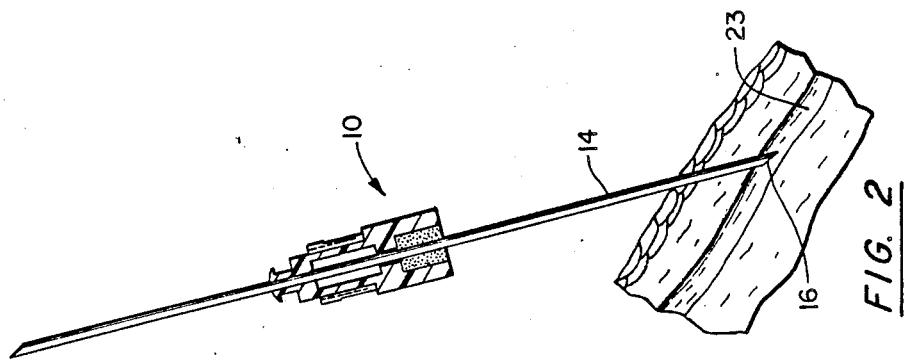
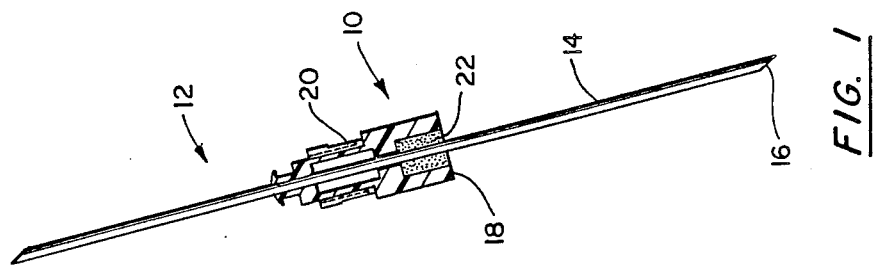

BLOOD VESSEL LOCATING NEEDLE ASSEMBLY WITH THERMOCHROMIC INDICATOR

BACKGROUND OF THE INVENTION

1. 1. Field of the Invention

The present invention relates to needle assemblies employed in the collection or dispensing of liquid samples and particularly to needle assemblies which provide a visual indication of the presence, within the bore of the needle, of a liquid having a temperature which differs from the local ambient temperature. More specifically, this invention is directed to the sampling of body fluid, for example blood, wherein a visual indication is provided when the sampling needle is in fluid flow communication with a blood vessel or other fluid filled part of the body of an animal. Accordingly, the general objects of the present invention are to provide a novel and improved apparatus and method of such character.

2. Brief Description of the Prior Art

While not limited thereto in its utility, the present invention is particularly well-suited for use in the collection of blood from a human patient. The provision of assurance that a blood connecting needle is, prior to an attempt to initiate the collection procedure, in fluid flow communication with a blood vessel constitutes a long-standing problem. In many situations, the nurse or clinician attempting to collect blood, or to administer a pharmaceutical, is uncertain, even with tourniquet pressure applied, whether vein entry has been achieved by the pointed distal end of a needle cannula. In the case of blood collection, if a vein is not penetrated, or if the needle passes completely through a thin vein, the nurse or clinician will have to search for a new vein. This is most uncomfortable for the patient and, where evacuated collection tubes are employed, often results in the evacuated tube losing its vacuum, thus requiring that a new evacuated tube be mated to the needle assembly. Many attempts to solve this problem, none of which have achieved widespread acceptance among the medical professionals, have been proposed.

For an example of state-of-the-art blood withdrawing devices which employ an evacuated collecting tube, reference may be had to U.S. Pat. Nos. 3,886,930 and 4,079,729. In the use of these patented devices, vein penetration is indicated when the evacuated tube and needle assembly are pushed together, thereby establishing fluid communication between the interior of the evacuated tube and the needle bore, by the flow of blood into the evacuated tube. Obviously, if blood does not enter the evacuated tube, vein penetration has not been achieved and the needle will have to be withdrawn and relocated.

In an attempt to reduce patient discomfort and a waste of evacuated collecting tubes, various vein locating indicators have been proposed. In one class of such indicators, a needle assembly is provided with a transparent chamber and the entry of blood into this chamber, prior to the joining of the evacuated tube to the needle assembly, will provide an indication of vein penetration. For examples of this approach, reference may be had to U.S. Pat. Nos. 3,585,984; 4,166,450; 4,436,098; 4 416,290; and 4,312,362. A major deficiency with this approach s that it adds significantly to cost of manufacture of the needle assembly and presents the possibility of a false indication, i.e., the failure of the chamber to fill may simply be a result of insufficient pressure differential, an air lock or a defective collection device. The added cost results from the fact that the needle assemblies require either a complex valving system and/or a chamber having an air permeable wall or membrane. Further, to be practical, needle assemblies of the type being discussed require the presence of a relatively large quantity of aspirated blood in order to permit the visual confirmation of vein penetration. The transfer of this quantity of blood into the indicator chamber, without a driving negative pressure mechanism such as an evacuated tube, presents a problem if an air-lock develops within the needle assembly or if the patient has a "weak" vein. Obviously, if the operator does not see aspirated blood in the indicator chamber, it may be incorrectly concluded that a vein has not been penetrated, thus leading to unnecessary and painful vein searching.

It is to be noted that use of transparent blood collecting chambers to indicate vein penetration has also been proposed for I.V. catheters. As an example of this technology, reference may be had to U.S. Pat. No. 4,108,175 wherein the added complication of mechanical means to create a negative pressure to draw blood into the transparent chamber is provided. The comments above with respect to the deficiencies of needles having transparent indicator chambers are generally applicable to catheters.

It has also been suggested that local tissue temperature can be measured and employed to position a fluid withdrawing device. For example, referring to U.S. Pat. No. 4,280,508, it has been proposed to employ a temperature sensing probe, located inside of the needle bore, which is removed from the needle assembly after positioning but prior to fluid withdrawal. The patented device is disclosed as being used in an amniocentesis procedure. Other suggestions for the use of a temperature probe within the bore of a needle, coupled with transmission of a signal commensurate with the sensed temperature to a remote location, may be seen from U.S. Pat. Nos. 4,476,877 and 4,665,927.

It has also been proposed to locate superficial and sub-superficial veins, for subsequent venipuncture, by sensing the temperature on the surface of a patient's skin. Thus, U.S. Pat. Nos. 4,015,591; 4,175,543 and 4,448,204 relate to the use of thermochromic liquid crystal mixtures which are applied to the patient's skin. In theory, the surface of the skin above a vein would be warmer than the surrounding tissue and this the vein pattern would be reflected by the color pattern observed in the liquid crystal containing coating which is in contact with the skin. In actual practice, however, this technique works only where the patient's veins are sufficiently large and close to the skin surface that the nurse or clinician can likely find and penetrate the vein without the liquid crystal "map".

SUMMARY OF THE INVENTION

The present invention overcomes the above briefly discussed and other deficiencies and disadvantages of the prior art by providing a novel needle assembly and method which clearly and unambiguously, and with minimal delay, provides a visual indication that fluid flow communication has been established with a blood vessel, or other fluid containing region of the body of an animal, via a needle cannula. Apparatus in accordance with the present invention couples the thermal conductive properties of a needle to a temperature responsive signal generator. The invention thus comprises a crystalline sensing indicator which is integral with, or attachable to, the needle assembly of a fluid dispensing or collecting device.

A needle assembly in accordance with the present invention typically has a metal cannula, the cannula having a pointed distal end and defining a hollow needle bore. The cannula passes through a needle hub and its proximal end may be attached to or is integral with a fluid dispensing or collecting device such as, for example, an evacuated tube. Depending on the application, the cannula may be discontinuous and will customarily be provided with a "valve", a pressure responsive flow controller located within the hub assembly for example. An energy sensing indicator, specifically a crystalline sensing indicator, is located at or near the needle hub and is in intimate contact with the metal cannula. The sensing indicator is configured to detect either thermal or mechanical changes within the cannula bore and to provide, directly or indirectly, a visually observable indication of such changes. In accordance with the preferred embodiment, the energy sensing indicator comprises thermochromic liquid crystals which, in response to the flow of aspirated blood into the bore of the needle when blood vessel penetration occurs, change color due to the transfer of thermal energy from the blood to the liquid crystals via the metal cannula.

BRIEF DESCRIPTION OF THE DRAWINGS

The present invention may be better understood and its numerous objects and advantages will become apparent to those skilled in the art by reference to the accompanying drawing wherein like reference numerals refer to like elements in the several figures and in which:

FIG. 1 is a schematic side elevation view, partly in section, of a needle assembly in accordance with a first embodiment of the present invention;

FIG. 2 is a view similar to FIG. 1 depicting the mode of operation of the apparatus of FIG. 1;

FIG. 3 is a schematic side elevation view, partly in section, of a needle assembly in accordance with a second embodiment of the present invention; and FIG. 4 is a schematic side elevation view, partly in section, of a needle assembly in accordance with a third embodiment of the invention.

DESCRIPTION OF THE DISCLOSED EMBODIMENTS

As noted above, while not limited thereto in its utility, the present invention is particularly well-suited for use in the collection of blood samples and, in this use environment, the needle assembly of the present invention will be associated with an evacuated collection tube. It is emphasized that the internal portion of the hub or housing 10 of a needle assembly in accordance with the present invention, the needle assembly being indicated generally at 12 in the drawing, has been shown schematically and may be modified commensurate with the particular application for which the needle assembly is intended. The needle assembly is depicted as employing only a single metal cannula 14 which extends through the hub 10. The needle assembly may, however, be comprised of a pair of axially aligned cannulas. The cannula 14 is, of course, provided with a hollow needle bore, has a pointed distal end 16 and is typically comprised of stainless steel.

In the embodiment of FIG. 1, the hub 10 comprises a body 18 which is molded from a transparent plastic such as, for example, polycarbonate. The body 18, at the end thereof which is closest to the pointed end 16 of cannula 14, is provided with a bore which, at least in part, has a larger diameter than the external diameter of cannula 14. Thus, a plurality of regions which extend coaxially with the cannula 14 may be defined in body 18 by ribs which securely engage the cannula 14. Alternatively, an annular space about cannula 14 may be provided which extends upwardly from the lower end of the body 18 as the needle assembly is depicted in FIG. 1, the portion of body 18 above this annular region securely engaging the cannula. Other arrangements are, of course, possible.

The body 18 of hub 10 defines an upwardly facing shoulder with a plurality of guide ribs or the like 20 for mating with an evacuated collection tube holder or the like. The evacuated collection tube is mated with the needle assembly after venipuncture is confirmed in the manner to be described below.

In accordance with a first embodiment of the invention, the annular region or the plural regions defined by spaced ribs about the cannula at the lower end of body 18 of hub 10 are filled with a mixture which comprises thermochromic liquid crystals as indicated at 22. The liquid crystals may be applied in solution with the solvent subsequently evaporating. The liquid crystal mixture will be in intimate contact with the steel cannula 14, i.e., a good heat exchange relationship will be established between the metal cannula and the liquid crystals. Accordingly, when a vein 24 is punctured as depicted in FIG. 2, and blood flows into the bore of the cannula, the increase in temperature will almost instantaneously be transmitted via the steel wall of the cannula to the liquid crystals. The liquid crystals will, also almost instantaneously, respond to the increase in temperature and will change color. This color change may be observed by the nurse or clinician through the transparent plastic hub and, when observed, the evacuated tube will be mated with the needle assembly and the blood collected. As an alternative construction, the voids which are provided to receive the liquid crystals may be omitted and the liquid crystals may be mixed with the hub resin to form a thermosensing hub.

The embodiment of FIG. 3 is similar to that of FIGS. 1 and 2 with the exception that the liquid crystals are supported on the cannula 14 below the hub 10 as indicated at 24. If necessary or desirable, the liquid crystal body 24 may be encapsulated in a transparent plastic film or resin and inserted over the cannula 14 as a separate element which may thereafter be integrated with the hub.

In the embodiment of FIG. 4, the hub 10 is provided with a recess 26 which extends all the way to the bore which receives the cannula 14. The liquid crystal mixture, indicated at 28, is inserted in the bore 26 and may thereafter be encapsulated by means of a transparent plastic insert or resin, not shown.

To summarize the functioning of the novel needle assembly of the present assembly, blood vessel penetration is visually indicated by a change in color of a temperature sensitive indicator located in heat transfer relationship with the needle shaft. Because of the high thermal conductivity of the needle shaft and the fact that its temperature is lower than that of the tissue when it is inserted, there is rapid heat transfer from the animal's tissues to the metal shaft during the insertion process. However, since the proximal end of the needle shaft is exposed to the ambient air temperature, which is lower than the tissue temperature, the high thermal conductivity of the needle shaft will cause the heat picked up by the distal end to be dissipated to the surrounding ambient air. Therefore, the temperature of the needle's proximal end will remain cooler than that of the inserted end while the needle shaft travels through the tissue en route to a vessel. When the needle's distal end penetrates a blood vessel, which has a higher fluid pressure than that present in the bore of the needle prior to insertion, blood will travel into the bore of the needle until an equalization of fluid pressure occurs. The preferred needle assembly is configured so that this equalization occurs at some point after the bulk of the needle bore is filled with entering blood. With the bore filled with blood, its heat will be rapidly transferred to the portion of the needle shaft displaced outwardly from the surface of the animal's skin, and subsequently to the temperature sensitive indicator, thus giving the operator a visual indication of vessel penetration.

Unlike the above-discussed prior art, a much smaller quantity of aspirated blood is needed to produce a visual indication of vessel penetration when employing the present invention. Accordingly, there is a much smaller chance of false negative indications. Additionally, if an air-lock occurs in the needle shaft the compressed air comprising the air-lock will function as a heat transfer conduit between that blood which does enter the needle shaft and the sensing indicator.

In accordance with the preferred embodiment of the invention, as noted above, the preferred cannula temperature indicator comprises thermochromic liquid crystals. These mesophasic color changing liquid crystals can be either cholestric or chiral nematic. Acceptable liquid crystal formulations will produce color plays in the range of 21°–37° C. The liquid crystal formulations may be applied directly to the needle assembly or incorporated into, onto, or under a polymeric material that is either attached or adhered to or is an integral component of the needle assembly. The liquid crystals can be applied or added as a paste, a neat liquid, a mixture, a solution, or as a micro encapsulated slurry or coating. Additional substances may be added to the liquid crystals to enhance the thermal, optical or compositional properties of the indicator. Thus, the liquid crystal mixture may include chemical binders, adhesives, color additives and dyes, light absorbers, light contrasting material, ultra violet stabilizers, thermal conductive material and volatile solvents. Those skilled in the art will recognize that the present invention may be incorporated into a variety of different needle assemblies with differing thermal conductive properties. Therefore, the liquid crystal formulation and thermochromic range are dependent on the design and composition of the individual needle assemblies.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method of detecting the penetration of liquid into the bore of a cannula comprising the steps of:
   establishing a heat transfer relationship between the cannula and a thermochromic crystalline material, the thermochromic crystalline material undergoing a change in color in response to an increase in its temperature; and
   visually observing the crystalline material to determine if the material has changed color in response to a temperature increase commensurate with the flow of bodily fluid into the cannula bore.

2. The method of claim 1 wherein the step of establishing a heat transfer relationship comprises:
   placing the thermochromic crystalline material in intimate contact with a portion of the exterior surface of the cannula.

3. In apparatus for sampling bodily fluid, said apparatus comprising a cannula having a distal end for penetrating a body and a proximal end, said cannula being comprised of a thermally conductive material and defining a bore, the improvement comprising:
   an element comprising a thermochromic crystalline material disposed in intimate heat transfer relationship with the exterior of the cannula at a position displaced from a distal end thereof, the thermochromic crystalline material having a color which is temperature dependent, and a hub member for supporting the cannula, the element comprising the thermochromic crystalline material being in abutting relationship with said hub member and encircling said cannula, the penetration into the bore of the cannula of a fluid having a temperature which differs from the initial temperature of the cannula resulting in the transfer of thermal energy between the fluid and the crystalline material whereby the crystalline material will undergo a color change.

4. The apparatus of claim 3 wherein the cannula is comprised of steel.

* * * * *